United States Patent [19]

Defebvre et al.

[11] 4,233,849

[45] Nov. 18, 1980

[54] METHOD FOR MEASURING THE FATIGUE OF A TEST-PIECE SUBJECTED TO MECHANICAL STRESS

[75] Inventors: André Defebvre, Lambersart; Jean Pouliquen, Santes, both of France

[73] Assignee: Agence National de Valorisation de la Recherche (ANVAR), Neuilly-sur-Seine, France

[21] Appl. No.: 9,827

[22] Filed: Feb. 6, 1979

[30] Foreign Application Priority Data

Feb. 16, 1978 [FR] France ................................ 78 04995

[51] Int. Cl.³ .............................................. G01N 3/32
[52] U.S. Cl. .......................................... 73/812; 73/579
[58] Field of Search ................ 73/812, 579, 787, 849, 73/851, 808, 810, 599, 645, 646

[56] References Cited

U.S. PATENT DOCUMENTS

| | | | |
|---|---|---|---|
| 3,854,325 | 12/1974 | Coate | 73/599 X |
| 3,940,973 | 3/1976 | Muscan | 73/826 X |
| 4,096,740 | 6/1978 | Sallee | 73/579 X |

*Primary Examiner*—Jerry W. Myracle
*Attorney, Agent, or Firm*—Robert E. Burns; Emmanuel J. Lobato; Bruce L. Adams

[57] ABSTRACT

A method for measuring the fatigue of a test-piece subjected to mechanical stress. The test-piece is stressed and pulses of ultrasonic waves are transmitted along the surface region of the stressed area and received. The acoustic attenuation of the waves, due to the fatigue caused by the stress, is measured and provides an indication of the amount of fatigue.

13 Claims, 9 Drawing Figures

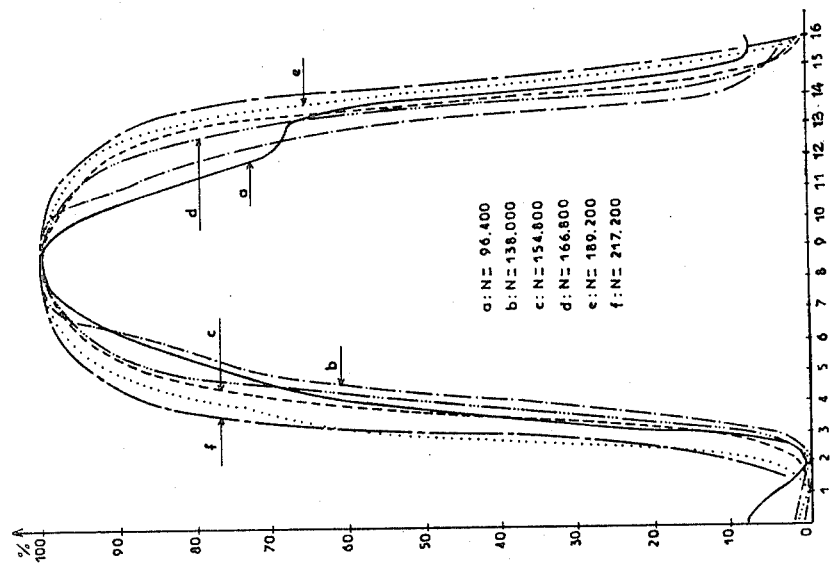
Fig.8
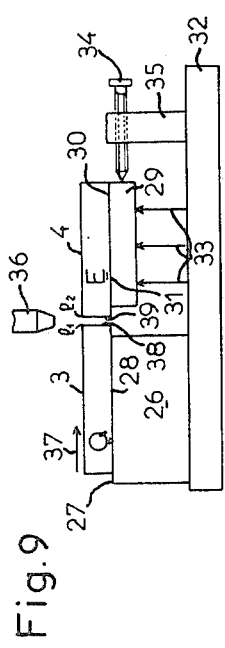
Fig.9
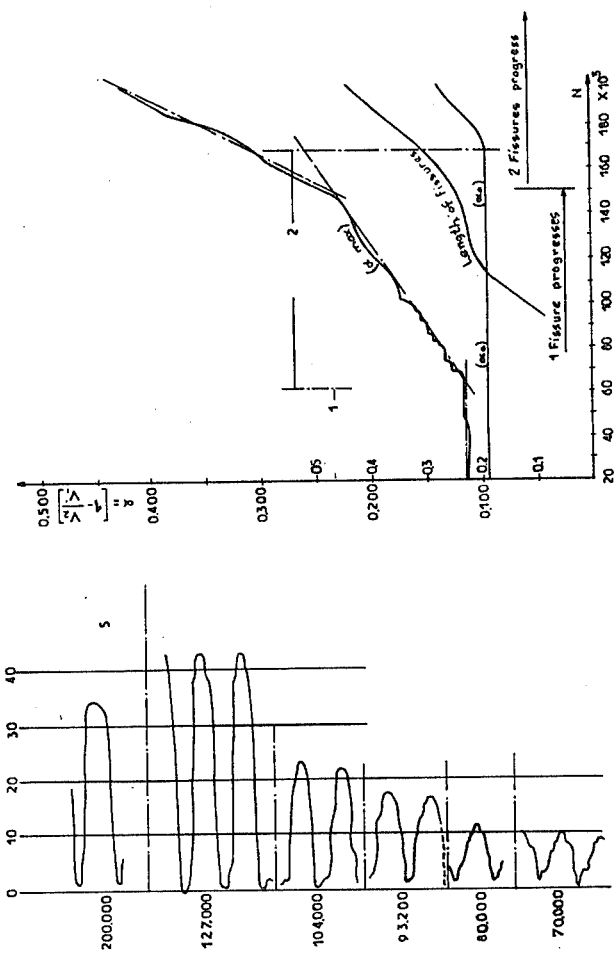
Fig.7
Fig.6

METHOD FOR MEASURING THE FATIGUE OF A TEST-PIECE SUBJECTED TO MECHANICAL STRESS

FIELD OF INVENTION

The present invention relates to a method for measuring the fatigue of a test-piece subjected to mechanical stress, as well as the elements allowing the method to be carried out: test-pieces, fatigue test machines, mounting of the arrangement.

BACKGROUND OF THE INVENTION

The beginning of fatigue cracks is a very localised surface phenomenon which frequently involves only the first layer of grains adjoining the surface.

Various works, namely that of FORSYTH shows that the beginning of cracks occurs from a polished surface in two stages: an initial stage during which there is plastic deformation of the surface and a propagation stage referred to as I which corresponds to the development of a microcrack by shearing in the first grain or grains underlying the surface.

The beginning of cracks is generally studied by metallography in spite of the excessively pinpoint nature of the observations made by this method, which is not suitable for observing the damage as a whole.

Attempts have been made for a long time to use acoustic, electromagnetic or holographic methods, without one of these methods providing absolutely new results as regards the starting mechanism.

In the field of acoustic methods, the properties of surface localisation of Rayleigh waves seemed to mark them out more particularly for this type of application. However, the tests made by TRUELL and CHICK using attenuation of Rayleigh waves remained without consequence, possibly due to the lack of sensitivity of their method (ultrasonic methods for the study of stress cycling effects in metals—NADD TR 60-920, April 1961). The same was true for the work of BROSSENS, HAKIMI and KHABBAZ, who worked at frequencies which were too low (2 MHz), ("Detection of fatigue damage with Rayleigh waves", August 1960-Technical Report 60-307, Applied Mechanics Laboratory, M.I.T. Cambridge, Massachusetts. Aeronautica Research Laboratory, Contract No. AF 33 (616) 6469 Project No. 7063, Task No. 70532).

The work carried out by the applicants has made it possible to remove most of the difficulties encountered in the use of surface waves and to propose a method for the detection of the phenomena of corrosion or fatigue cracking of metals by studying variations in the propagation or attenuation speed of Rayleigh waves.

In particular, this work has underlined the fundamental advantage of the acoustic attenuation parameter for measuring fatigue. However, if the method recommended in this way, namely a method of forming a loop from undamped surface waves of high frequency, of the order of 20 MHz, has proved very sensitive, making it possible to measure variations in the speed of the phase of Rayleigh waves as low as $10^{-6}$ and variations of attenuation of some 0.001 dB, it had many drawbacks.

First of all, it was discontinuous, the measurement of the acoustic attenuation taking place in the inoperative state, on the test-piece in the position of maximum stress.

This method has also proved difficult owing to the necessity of careful stabilization of temperature to within 1°/100° C., the loop frequency being very sensitive to temperature and to the necessity for strict control of the quality of production of pure progressive Rayleigh waves, any parasite reflection in this looping method disturbing the measurements. The solution of these problems necessitated a considerable amount of electronic equipment, high performances and the permanent presence of a highly skilled operator.

Finally, interpretation of the results was difficult since the two quantities measured, namely variations of frequency and attenuation, were connected.

SUMMARY OF THE INVENTION

Continuation of the research has made it posible to develop a method no longer having these drawbacks and which constitutes one of the objects of the present invention.

According to this new method, the acoustic attenuation parameter, indicative of fatigue, is measured continuously, with varying degrees of stress on the test-piece, by using acoustic pulses in a completely automated process.

An advantageous feature of the invention with respect to the looping method used previously is to propagate the ultrasonic waves in an open circuit in order to achieve a measurement of acoustic attenuation, with comparable accuracy, at any degree of stress.

This method according to the invention consists essentially of causing the propagation, in the samples studied, of trains of high frequency acoustic waves of adjustable amplitude in order to collect trains of waves of lower amplitude delayed by the time taken for propagation of the acoustic waves, the attenuation being expressed by the ratio of the amplitude of the waves emitted to that of the waves received.

The fact of working with pulses makes it possible to eliminate stationary waves and to minimize the effect of parasites by making the system "deaf" at certain instants.

Direct measurement of the ratio defining attenuation relieves the waves emitted from the constraint of stabilizing the amplitude and the delay in reception in relation to emission makes it possible to treat the two terms of the ratio with the same electronic equipment, which eliminates the drawbacks of shunting. It is also apparent that the attenuation defined in this way is only slightly sensitive to temperatures and the precautions which were indispensable for carrying out the author's first method are greatly simplified.

Furthermore, the short period of time for acquiring a measurement makes it possible, by varying the rate of emission of the acoustic pulses depending on the degree of stress on the test-piece, to carry out the measurements "as they present themselves" for any degree of stress, even in the case of the application of rapidly varying stress and to make use of all the resources of information.

In particular, for each state of stress on the test-piece, it is possible to calculate the average of the attenuations measured during numerous successive cycles and to memorize or edit solely significant measurements while eliminating erroneous measurements (too different from the former) or redundant measurements (equal to the former).

Finally, the use of an internal clock makes it possible to extend the method to "static" measurements for stress on the test-piece which is constant over a period of time.

The method according to the invention, for measuring the fatigue of a test-piece subject to stress, by measuring the acoustic attenuation of ultrasonic waves, is characterized in that stress is applied to the test-piece, in that one causes the propagation in an open circuit of ultrasonic pulses of predetermined frequency along the test-piece, at any degree of stress and in that the acoustic attenuation of said pulses is measured.

BRIEF DESCRIPTION OF DRAWINGS

The invention will be better understood on referring to the ensuing description, relating to a non-limiting embodiment using flat unidirectional bending and surface ultrasonic waves, as well as to the accompanying drawings which form an integral part of this description.

FIG. 6 shows portions recording the attenuation at various degrees of fatigue, in the case of a practical measuring example.

FIG. 7 shows, in this same example, variations of attenuation at maximum bending ($\alpha$ max) and at zero bending ($\alpha$ o) as well as the propagation of the length of crack, measured on photographs taken in the inoperative state, in the position of maximum bending, as a function of the number N of bending cycles.

FIG. 8 indicates the variation of attenuation during a bending cycle $\alpha$ (F), defined by F=16 points, with varying degrees of fatigue.

FIG. 9 is a diagrammatic view, in side elevation, of a mounting bench used for securing to the bending test-piece, the quartz or other piezo of ferro-electric components, respectively an emitter and receiver for surface acoustic waves.

DESCRIPTION OF PREFERRED EMBODIMENTS

Figure 1:
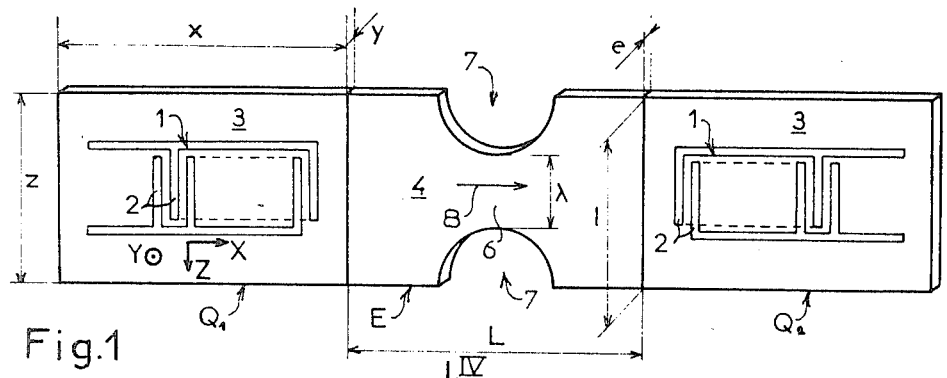
FIG. 1 is a perspective view illustrating the test-piece preferably used for carrying out the method according to the invention, provided with devices, respectively an emitter and receiver for acoustic waves.

In the measurement, where it is well known that, when a test-piece is subjected to flat bending, the fatigue phenomena firstly manifest themselves in the superficial regions subject to maximum extension or compressive stress, it is proposed according to the invention to follow the development of this fatigue by continuous measurement of the attenuation of an acoustic Rayleigh wave (referred to hereafter as "OR") spreading out on the surface subjected to elongation of a flat steel test-piece subjected to a regime of unidirectional bending.

This choice of stress imposes on the surface, the appearance of cracks to be investigated acoustically. Furthermore, the adoption of an OR frequency of 20 MHz approximately limits the depth investigated to approximately 75 $\mu$m for steel, owing to their practical depth of penetration of approximately half the length of an acoustic wave $\Lambda/2$. Finally, since the time for the passage and measurement of acoustic waves ($\leq 50$ $\mu$sec) remains short compared with the period of mechanical stress 20 m.sec at 50 Hz), measurement of the attenuation may take place as it happens at numerous points of the bending cycle (at least 100). For their part, the applicants are limited to a maximum of 16 points per cycle, which seems quite sufficient.

Since their prior work has established that variations in the acoustic attenuation during the first stages of fatigue—appearance and propagation of micro cracks, remain limited to several decibels, the system has been designed to detect variations of attenuation of some 0.01 db with equivalent measuring stability over 48 hours. The ultimate stages of fatigue leading to the destruction of the sample are thus excluded from the practical study according to the invention.

The principle of measurement according to the invention will now be described with reference to FIG. 5, which illustrates an example of a system for carrying out the method according to the invention.

Trains of high frequency waves of adjustable amplitude $V_1$ and having a duration of 5 to 15 $\mu$sec, coming from a high frequency generator, appropriately modulated (m) and amplified ($A_1$), are supplied to the emitter comb $Q_1$ of an O.R. transducer quartz. After propagation on the sample studied E and conversion by the receiver quartz $Q_2$, one obtains an output signal of amplitude $V_2$ retarded by the period of time $\tau$ for propagation of the signal emitted. The attenuation will be characterised by the ratio $V_2/V_1$ or even better by $V_2(t+\tau)/V'_1(t)$, $V'_1(t)$ being a known fraction of $V_1(t)$, having a slightly higher level than $V_2$ obtained by a graduated attenuator comprising a keyboard which can be adjusted in jumps of 0.1 db from 0 to 101 db. Therefore, it is unnecessary to stabilize the level $V_1$, possible fluctuations of which will now impede the measurements.

The signals $V'_1$ and $V_2$, of substantially trapezoidal shape, occur successively over a period of time and may be processed by the same measurement system. They are firstly amplified in a linear manner ($A_2$), detected (D), re-amplified ($A_3$), then calculated by a rapid analog digital (A/D) converter (conversion time: 4 $\mu$sec). An attached circuit, triggered by the selector (S) whose function will be described hereafter, supplies two conversion control pulses $I_1$, $I_2$ of adjustable position. The latter are adjusted, after display on the oscilloscope, with respect to $V'_1$ and $V_2$ such that the conversion takes place on the peak values of these signals.

In order to increase the stability of the system and to minimize the possible presence of parasite pulses, one undertakes the addition of 50 respective values of $V_2$ and $V'_1$, corresponding to the same bending state in 50 successive periods, before effecting the simple operation $$\alpha \left( = I - \frac{50\ V_2}{50\ V_1'} \right)$$

the result of which is given in a three-figure number.

Since the values of $V_2$ and $V'_1$ have been chosen to be similar, the attenuation measured can be converted directly into decibels, in fact:

$$A_{db} = 20\log \frac{V_1'}{V_1' - \Delta V} \simeq \frac{20}{2.30} \text{Log}\left(1 + \frac{\Delta V}{V_1'}\right) \simeq$$

-continued $$10\frac{\Delta V}{V_1'} = 10(1 - \frac{V_2}{V_1'})$$

The corresponding remains suitable up to an attenuation of approximately 3 db. Beyond this, it is easy to undertake the conversion:

$$A_{db} = -20 \log(1-\alpha)$$

Once the attenuation of a state has been achieved, the selector switches in sequence to the analysis of the following state.

Several types of digital or analog outputs for information have been provided in the example illustrated.

A digital display unit has been provided using photoluminescent diodes, which is particularly useful at the time of preliminary adjustments where a keyboard comprising three keys selects the display, by means of these photoluminescent diodes, of the values $V'_1$, $V_2$ and of the result of the calculation $$\alpha = (1 - \frac{V_2}{V_1'}).$$

An analog output has also been provided, via a digital/analog (D/A) converter, facilitating decoding of the calculation. Two methods of recording the resulting analog voltage are possible, on a recorder having an input impedance of $Z_e \geq 10 \text{ k}\Omega$, full scale sensitivity of 1 volt, namely a total recording to three figures and a partial recording to the two lower figures.

The total recording makes it possible to follow overall the development of the attenuation with regard to time. However, an automatic change of range makes it possible to improve the sensitivity during the first stage of studying fatigue, during which the attenuations at all points of the bending cycle remain very similar.

The limits of the four ranges retained for the attenuation are respectively:

$$0 < \alpha_1 < 0.099; \; 0.1 < \alpha_2 < 0.199$$
$$0.2 < \alpha_3 < 0.399; \; 0.4 < \alpha_4 < 0.999$$

Since the evolutions of attenuation are monotone, automatic changes of sensitivity can be easily interpreted on the recording.

The partial recording makes it possible to follow with increased sensitivity the slight development of fatigue of a small number of particular bending states. Although it is more accurate, this method of recording is less representative of the total developmemt of fatigue, following of which may be complicated by overlapping of the curves recorded.

A digital output is also provided on a printout (I).

To this end, the measurements corresponding to the bending states retained per cycle are memorised (M) in suitable addresses defined by the selector (S). They are printed, for a given state, solely if they are identical twice in succession with a value different to that of the last print-out (validation V). One thus eliminates both erratic variations due to possible parasite pulses as well as the inevitable redundant information in a study of this type. In fact, it will be recalled that at a rate of one measurement every 50 cycles, for a fatigue study relating to $5.10^5$ bending cycles, in these tests, it would be necessary to carry out $10^4$ measurements.

However, every ten thousand cycles, a systematic output of the measurements of the 16 bending states, is provided in order to make it easier to trace the curves of development of attenuation for the various bending states F depending on the fatigue. On the other hand, inhibition of the printing tests allows the continuous output of all results. Each print-out comprises an indication of the values:

of the number of bending cycles T (in thousands of revolutions)
of the bending state F ($1 \leq F \leq 16$)
of the attenuation
For example: T 152; F 14; 0.123.

An outer digital output is finally provided via an "outer" connector (not shown) located upstream of the print-out validation V, in order to allow the systematic output of the above data in BCD code for possible interconnections with a tape perforator or a computer for the purpose of actual time or delayed processing at the user's discretion.

Figure 5:
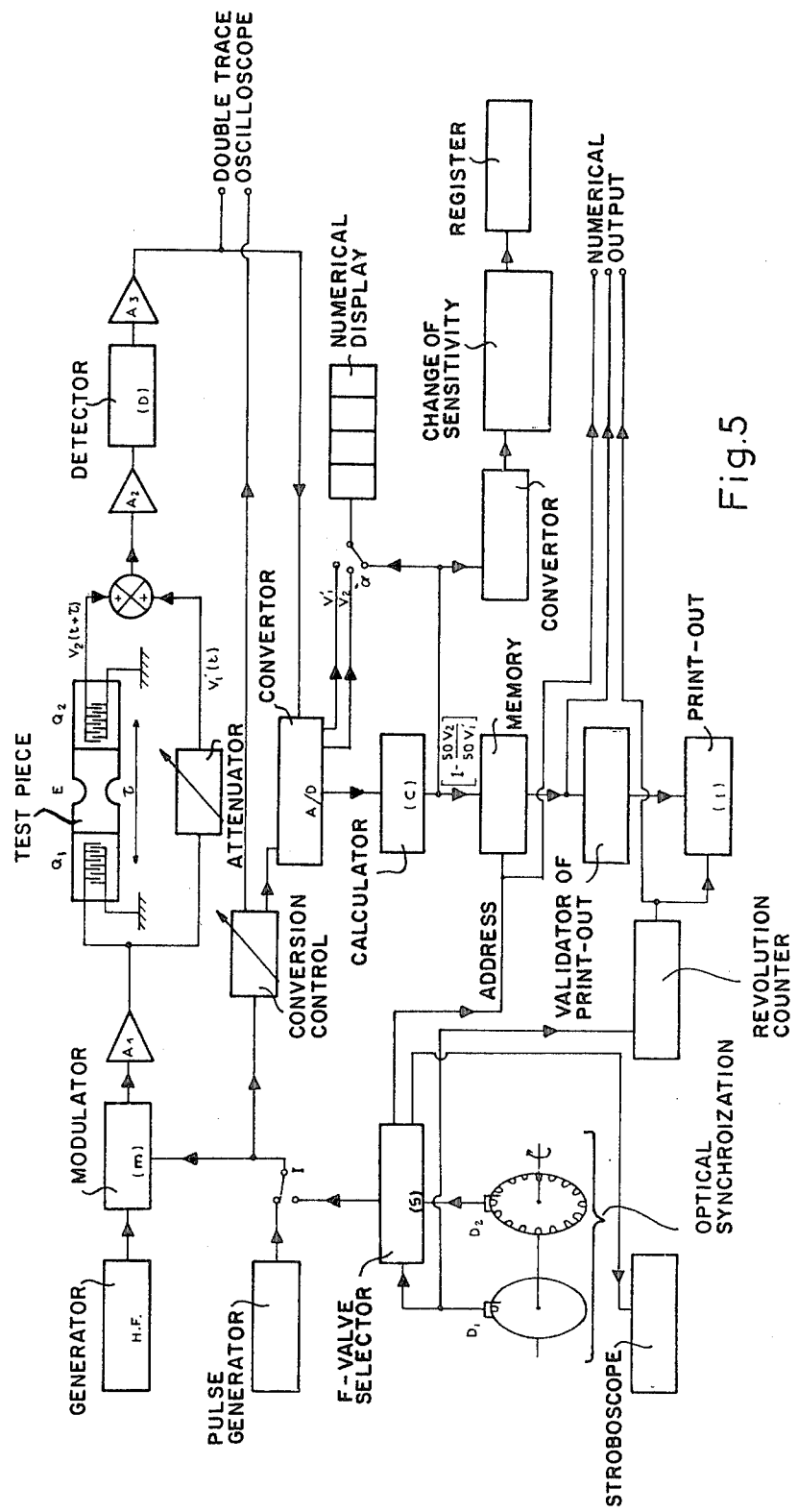
FIG. 5 illustrates the wiring diagram of a measuring system.

The measurement system shown diagrammatically in FIG. 5 also comprises accompanying control mechanisms whose essential object is to facilitate preliminary adjustments or to synchronize the measurement operations with the mechanical bending stress E applied to the test-piece.

Control of the modulator (m) may be achieved by an incorporated pulse generator. It is also possible to undertake static measurement of the attenuation for any bending positions at the time of preliminary adjustments.

The modulator (m) may also be controlled by two types of optical signal emanating, in the example illustrated, from perforated discs $D_1$ and $D_2$ connected to the shaft of the bending machine.

The synchronization signal ($D_1$) defines the beginning of each period.

The choice of the number F of measuring points and their position on a bending cycle takes place by means of the disc $D_2$ and by display on a coding wheel (0 to 15). If the number of notches F corresponds to the number displayed (F-1), one analyses all the states corresponding to the notches of $D_2$. If $p < F - 1$ is displayed on the coding wheel, the (p+1) positions are analyzed in sequence, which positions occur after the synchronization pulse from $D_1$.

The electronic selector controlled by the discs $D_1$ and $D_2$ and the coding wheel carries out addressing of the memories for the accumulation of the results and triggering of the stroboscope allowing visual observation of the bending state under a dynamic regime. The number of pulses $D_1$ added by a revolution counter (CT) is available (in thousands of revolutions) at the time of the display.

The acoustic system and the bending machine will now be described respectively with reference to FIG. 1 and with reference to FIGS. 2 to 4.

The reciprocal electrical/mechanical conversion is carried out in the example illustrated by piezo electric quartz blocks provided with interdigital combs. The surface wave generated by the quartz $Q_1$ is transferred to the sample E to be studied, then once more received on a quartz $Q_2$ identical to $Q_1$ (see FIGS. 1 to 5).

Naturally, the piezo-electric quartz $Q_1$ and $Q_2$ could be replaced by any other piezo-electric or ferro-electric material.

The test-piece E is fixed so that no stress is applied to the acoustic transfer regions and so that the propagation of surface waves is not disturbed.

As shown more particularly in FIG. 1, the quartz blocks used, such as $Q_1$ identical to $Q_2$, of height Y and for example of dimensions x=30 mm y=2 mm and z=20 mm are provided, by photogravure with electrodes comprising a layer of aluminum deposited by evaporation under vacuum, with interdigital combs 1 comprising 70 pairs of teeth 2 parallel to the crystallographic axis Z and contained in the plane XOZ.

The distance between two teeth of the same parity, equal to the wave length $\Lambda$ of the surface wave generated, defines the frequency proper of the combs $F=V/\Lambda$: or for example F=17 MHz if $\Lambda=186$ $\mu$m with V=3153 m/sec.

The transfer of the acoustic wave is ensured by a technique of alignment of planes: the quartz $Q_1$ and $Q_2$ and the test-piece E are fixed end-to-end, along their edges, with a very slight thickness of fast-setting adhesive, so that the surfaces for the propagation of waves, namely the faces 3 of the quartz $Q_1$ and $Q_2$ comprising the combs 1 and one face 4 of the test-piece E undergoing maximum extension, at the time of bending of the latter, are co-planar.

The surfaces in contact are polished and have an acute angle (rounded portions less than 2 or 3 $\mu$m) and if one wishes to follow the fatigue of the test-piece by photography, it is preferable to ensure mirror-like polishing of its surface 4.

Alignment of the planes conveniently takes place under a metallurgical microscope with the assistance of a mounting bench such as that shown diagrammatically in FIG. 9. This mounting bench comprises a stand 26 having a flat and horizontal upper face 27 able to receive the quartz Q, i.e. $Q_1$ or $Q_2$, by a face 28 of the latter parallel to its face 3.

The mounting bench also comprises a table 29 having an upper face 30 suitable for receiving the test-piece E by a face 31 of the latter parallel to its face 4. Since the stand 26 is supported in a stationary manner by the frame 32 of the mounting bench, for its part, the table 29 is adjustable on the one hand as regards the vertical level and as regards horizontality of its upper face 30, this is by means of a set of vertical screws 33 able to be screwed at will to a greater or lesser extent in the frame 32 and on whose upper end the table 29 rests and on the other hand as regards spacing with respect to the stand 26, by the set of horizontal screws 34 able to be screwed to a greater or lesser extent in a projection 35 of the frame 32 located opposite the stand 26 with respect to the table 29, the end of the screws 34 closest to the stand 26 bearing against the table 29 opposite this stand 26. There are preferably two screws 34 for facilitating the orientation of the face 30 in a horizontal plane.

The mounting bench also comprises a metallurgical microscope 36 located above the latter, vertically above an area intermediate between the stand 26 and the table 29, vertically above the tops $1_1$ and $1_2$ of the edges 38 and 39 respectively of the face 3 of the quartz Q and of the face 4 of the test piece E to be made to coincide.

The mounting procedure is as follows:

The quartz Q, i.e. $Q_1$ or $Q_2$ is fixed to the stand 26 and the test-piece E is fixed to the table 29 by suitable means. Since the quartz Q and the test-piece E do not come into contact and the distance between their edges 38 and 39 to be assembled is of the order of 0.2 to 0.3 mm for example, by means of the screws 33, the tops $1_1$ and $1_2$ of the opposing edges 38 and 39 are brought into a position where they can be seen quite clearly over their entire length by means of the microscope 36, for example with maximum magnification of 500. By acting on the screws 34, the edges 38 and 39 are thus brought into contact. Observation in low light in the direction of arrow 37 of the image by reflection on the suitably polished faces 3 and 4, of vertical lines, makes it possible to check the alignment of the planes.

The edges 38 and 39 are then stuck with adhesive which sets immediately, having sufficiently low viscosity in order that, when applied to the faces 3 and 4 at the junction point of the edges 38 and 39, it penetrates the latter. The application of adhesive to the junction point of the lower faces respectively 28 and 31 of the quartz and of the test-piece E is recommended.

After several minutes for drying, it is possible to proceed with the mounting of the second quartz Q.

It should be noted that differences in level of several $\mu$m between the planes of the faces 3 and 4 are tolerable, the increase of the transfer losses not preventing the operation of the system.

Figure 2:
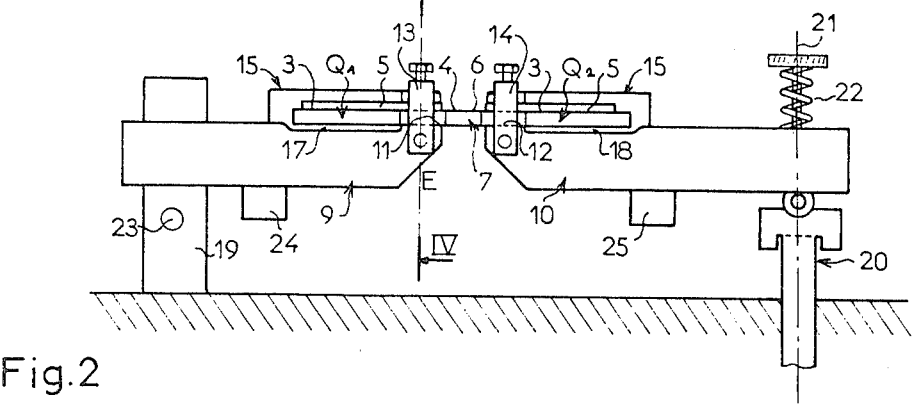
FIG. 2 is a view in side elevation of the bending machine preferably used for carrying out the method according to the invention.
Figure 3:
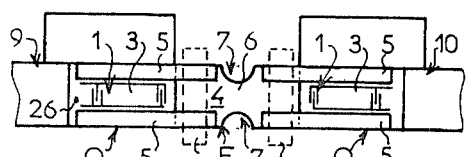
FIG. 3 is a plan view of the mounting of the test-piece on the bending machine.
Figure 4:
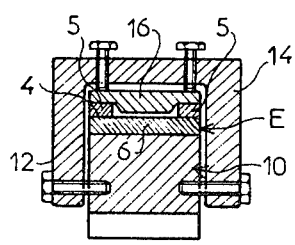
FIG. 4 is a sectional view along the plane IV—IV of FIG. 2.

The assembly of the test-piece E and of the quartz $Q_1$ and $Q_2$ is reinforced as regards its mechanical rigidity by metal bars 5 stuck laterally in an overlapping manner on the faces 3 and 4 respectively of the quartz $Q_1$ and $Q_2$ and of the test-piece E (see FIGS. 2 to 4).

In order to absorb the Rayleigh waves and possible volume waves, it is possible to provide various coatings on the quartz $Q_1$ and $Q_2$ on their face opposed to the face 3 supporting the combs, on this face 3 and on their edge beyond the combs with respect to their edge in contact with the test-piece E. For this purpose, it is possible to use adhesive tapes in particular.

The test-piece E could have various shapes.

A preferred shape is illustrated in particular in FIG. 1, according to which the test-piece E is flat, in the form of a rectangular parallelepiped of length L, arranged in the direction O X of the quartz $Q_1$ and $Q_2$ when the latter are assembled, a width l arranged in the direction O Z, these dimensions L and l defining the dimension of the face 4 of the test-piece to be studied and a thickness e measured in the direction O Y of the quartz.

The test-piece E has a recess at 7, at a mid-point of its faces having dimensions L×l in order to give the area 6 in which cracks occur a width $\lambda$ less than l and which defines the width of the acoustic field on the face 4 of the test-piece.

It is appropriate, but not imperative, that the width l of the test-piece is equal to that of the transducer quartz $Q_1$ and $Q_2$. The depth e should be greater than 10$\Lambda$, or 1.76 mm in steel at F=17 MHz and the length L is preferably of the order of 3 to 6 cm in order to limit the acoustic propagation attenuation.

Good results have been obtained using a test-piece E having the following dimensions: L=30 mm, l=20 mm, $\lambda$=5.9 mm, e=2 mm.

The dimensions of the bars 5 are such that they do not constitute a hindrance to the propagation of acoustic waves on the faces 3 and 4. They are located respectively on either side of the recess 7 parallel to the direction of propagation 8 of the waves on the face 4 of the test-piece E, from the quartz $Q_1$ towards the quartz $Q_2$. They are spaced apart at right-angles to this direction 8 by a distance greater than $\lambda$ and, naturally, greater than the corresponding dimension of the combs 1.

The assembly which has been described is mounted on a bending machine in order to undergo unidirectional bending, in a plane at right-angles to the face 4 and parallel to the direction 8, of chosen amplitude.

The machine used as an example by the inventors is illustrated diagrammatically in FIGS. 2 to 4.

The machine illustrated comprises two rigid bars 9 and 10, for example of brass, each of which is intended to bear by a flat surface respectively 11 and 12 against the face 31 of the test-piece E opposite its face 4 in an area of this face located between its recessed area 7 and its edge integral with a quartz, respectively $Q_1$ and $Q_2$. When the machine is inoperative, the contact faces 11 and 12 are coplanar.

Clamping of the test-piece E on the faces 11 and 12 of the bars 9 and 10 is ensured by clamping members 13 and 14 respectively which act on the mounting bars 5, in the direction of the support faces 11 and 12 respectively. Pressure is not applied directly to the bars 5, but through the intermediary of a member 16 which ensures electrical screening of the areas of the test-piece located respectively between each of the quartz $Q_1$ and $Q_2$ and the recessed area. This member 16 does not come into contact with the face 4 of the test-piece where the surface waves spread out. Screening of the other parts is ensured by means of metal covers 15.

It should be noted that the quartz $Q_1$ and $Q_2$ are supported solely by the fact that they are stuck to the test-piece E, the bars 9 and 10 comprising a recess 17 and 18 respectively, in facing relationship to these quartz, in order that these quartz are not subject to any mechanical stress at the time of bending of the sample.

In order to ensure this bending, the bar 9 is fitted in a stationary support 19, the bar 10 supported by this bar 9 via the sample E at one end is at the other end supported in a direction 21 for example at right-angles to the support face 11 and beyond the support face 12 with respect to this face 11, by a pin 20 able to move up and down in this direction 21 with respect to the stationary support 19, resulting in bending of the test-piece E, which ensures the connection between the movable bar 10 and the stationary bar 9 and which is connected rigidly to both of these bars.

The pin 20 is moved for example by a cam which is not shown, opposite a coil spring 22 also acting in the direction 21.

Naturally, other embodiments of the bending machine and associated device described above, for producing synchronization signals, could be envisaged without diverging from the scope of the invention.

It is nevertheless necessary to observe certain precautions: in particular, it is important that the acoustic transfer regions are not subject to any stress, which is ensured in the example illustrated by the presence of recesses 17 and 18 allowing the quartz to float and by the positioning of the clamping members 13 and 14 with respect to the junction points of the quartz/test-piece.

It is also wise to respect certain conditions as regards stability of temperature, which are not too critical in this case. Thus, in the example illustrated, water cooling 23 is provided for the mounting of the bar 9 in the stationary support 19 and means 24 and 25 for heating the bars 9 and 10 respectively are provided with control by way of a thermistance 26 placed in contact with the face 3 of one of the quartz $Q_1$ and $Q_2$.

In the example illustrated, the side of the test-piece E supporting the emitter quartz $Q_1$ is connected to the bar 9 and the side supporting the receiver quartz $Q_2$ is connected to the bar 10, but the reverse arrangement could also be adopted.

The method of connecting the composite line $Q_1$-E-$Q_2$ to the measurement system and its adjustment are within the scope of a man skilled in the art and consequently will not be described further. Adjustment of the attenuator is such that the value of $V'_1$ is slightly greater than the value of $V_2$ under static conditions.

Before carrying out a cycle of measurements, the discs $D_1$ and $D_2$ are put in position such that no notch in $D_2$ coincides with the notch in $D_1$ (see FIG. 5).

The coding wheel is made to display the number F ($0 \leq F \leq 15$ in the example illustrated) defining the number of measuring points per bending cycle of the test-piece E retained from those which $D_2$ makes possible, namely: 0 for 1 point and, generally, $n-1$ for n points.

During static operation, one undertakes adjustment of the conversion control pulses $I_1$ and $I_2$ with respect to the signals $V'_1$ and $V_2$, mentioned above, in order that the conversion takes place at the peak values of these signals $V'_1$ and $V_2$.

The measurement system is then left to operate for at least half an hour in order to obtain stable operating conditions.

After preliminary tests, the system may operate dynamically without surveillance.

However, it should be noted that it is still possible, after stopping the bending machine, to undertake measurements in a static manner in order to measure the values of $V'_1$, $V_2$ and $\alpha = 1-(V_2/V'_1)$ in a bending position, as desired, or to proceed with visual or photographic examinations of the face 4 of the test-piece E. These controlled stoppages disturb neither the progress of F nor counting the number of revolutions T.

However, in the course of taking measurements, one is prohibited from modifying the frequency of the oscillator, the adjustment of the adaptation of the combs and the position or form of the conversion pulses. If one of these operations were to be carried out, one could nevertheless compare the results obtained before and after the incident by proceeding with a static test, on the zero bending state, in order to note the possible sudden jump in the attenuation value which, resulting from the modification of adjustment of the measuring system, could not be considered as indicating fatigue.

As a concrete illustration of the method according to the invention and as a non-limiting example, bending tests were carried out on a test-piece of XC55 steel having dimensions of L=30 mm, l=20 mm, $\lambda$=5.9 mm, e=1.92 mm, cut from a bar having a diameter of 40 mm, at right-angles to the axis of this bar.

Mounted as afore-mentioned, this test-piece E was subjected to unidirectional bending having an amplitude of 1.7 mm at the level of the pin 20 (see FIG. 2), causing rupture at the end of 270,000 cycles.

The curve of FIG. 6 shows portions recording the attenuation at various moments of the fatigue.

The curves of FIG. 7 indicate variations of attenuation at maximum bending ($\alpha$ max) and at zero bending ($\alpha$ o) as well as an increase in the length of crack, measured from photographs taken at the time of a stoppage, in the position of maximum bending, as a function of the number N of bending cycles. Three stages of development are noted.

First Stage (N<60,000 cycles)

Attenuation at zero bending $\alpha$ o remains constant and that of maximum bending remains slightly greater (variation—0.2 db) and develops in small but numerous sudden jumps.

Second Stage (60,000 cycles<N$\lesssim$170,000 cycles)

Attenuation in the bent position α max progresses more rapidly and passes from progression in jumps to continuous progression with a given slope, whereas αo remains unchanged.

The slope of α max may be correlated with the spreading of a crack or cracks. In particular, it increases suddenly when a second crack begins to progress.

Third stage (N>170,000 cycles)

When the relative length of the crack reaches 30% of the useful width λ of the test-piece, attenuation at zero bending α o begins to increase in turn, possibly due to a deformation of the edges of the cracks, which no longer close-up completely.

The print-out makes it possible to trace with great accuracy the variation of attenuation during a bending cycle α (F), defined by F=16 points, at various degrees of fatigue.

Several curves, standardised to a constant height, are shown in FIG. 8. One will note a progressive enlargement of the curves: the attenuation approaches the maximum relative value (100%) with increasingly lower degrees of bending, when the number N increases.

In this test, where the first few thousand cycles have not been observed, it seems that:

in the absence of micro-cracks, attenuation remains constant for a given state of bending.

the appearance of the first micro-cracks is a sudden phenomenon causing a progression of the attenuation in jumps, the phenomenon being detected in the best way in the position of maximum bending.

At zero bending, the cracks are re-closed and not detected at least for a certain period of time.

the continuous development of attenuation should be able to be attributed to the appearance of a large number of micro-cracks per recording cycle (50×16=8,000 bending cycles) or to the continuous progression (length and depth) of existing cracks.

widening of the curve α (F) when N increases seems to translate the increase in the opening time of the cracks, whereas changes in the slope α max, when N increases, are linked with the number of cracks in the course of spreading.

These results confirm that Rayleigh waves are a valuable tool for observing fatigue in metals. Use of the method employing pulses according to the invention abolishes experimental difficulties (continuous presence of operators, stopping the fatigue for control measurements) and interpretation of the looping method used hitherto, thus giving rise to an automated process also facilitating analysis on an actual time or delayed time calculator. This major progress makes it possible to envisage exploitation programs intending to clarify the concept of damage as a function of the following parameters:

(a) influence of the number of cycles N.
(b) influence of the stress frequency.
(c) influnece of the shape of the stress cycle (square wave, saw teeth, generated with a vibrating box or mechanically) and possible overloads.
(d) respective influence of cold hardening and corrosion.

Naturally, the method, the test-piece, the methods of producing surface waves and constructing the bending machine and mounting bench as well as the electronic processing, which have been described, may be subject to numerous variations not diverging from the scope of the invention.

Finally, the method according to the invention, using surface waves in the example described, could be extended to the use of volume waves and other types of mechanical stress.

What is claimed is:

1. A method for measuring the fatigue of a test-piece subjected to stress by measuring the acoustic attenuation of ultrasonic waves, comprising affixing to said test-piece ultrasonic transmitting and receiving means at opposite sides respectively of an area of said test-piece to be stressed, applying stress to the test-piece in said area, propagating ultrasonic pulses of predetermined frequency in an open circuit along the test-piece from said transmitting means to said receiving means at different degrees of stress, measuring the acoustic attenuation of said pulses, and evaluating said attenuation in terms of fatigue.

2. A method according to claim 1, carried out continuously while causing, as the stress progresses, the propagation in the open circuit of the ultrasonic pulses of predetermined frequency along the test-piece, in a rhythmic manner depending on the degree of stress on the test piece.

3. A method according to claim 2, in which stress is applied to the test-piece cyclically, the propagation of the ultrasonic pulses is in a rhythmic manner depending on the degree of stress, according to an identical cycle or a cycle adapted to the stress cycle, as the latter progresses, the acoustic attenuation of said pulses being measured for each cycle and each degree of stress, and an average is produced of the measurement corresponding to the same degree of predetermined stress of the test-piece.

4. A method according to claim 1, in which the said ultrasonic waves are surface waves, and the stress is a bending stress.

5. A test-assembly for measuring the fatigue of a metal test-piece in bending, comprising a metal test-piece, an ultrasonic transmitter affixed at one end of said test-piece and an ultrasonic receiver affixed at an opposite end of said test-piece, said test-piece having at least one flat face intended to be arranged perpendicular to the direction of bending and defining an acoustic field, said face comprising a recess defining an area of preferred bending or maximum stress and cracking of predetermined width, measured in a direction intended to be placed at right-angles to the direction of movement of ultrasonic waves from said transmitter to said receiver, equal to the width of the acoustic field.

6. A test-assembly according to claim 5, having the shape of a flat rectangular parallelepiped whereof one of the major faces defines the acoustic field, and the said test-piece having two opposed notches in its two longest parallel edges in order to define the said recess.

7. A test-assembly according to claim 5 or claim 6, in which said test-piece has square ends perpendicular to said flat face, and in which said ultrasonic transmitter and receiver comprise quartz blocks adhesively affixed to said ends of said test-piece.

8. A test-assembly according to claim 7, in which said quartz blocks have faces coplanar with said flat face of said test piece.

9. A test-assembly according to claim 8, in which said quartz blocks have electrodes comprising interdigital combs on said faces which are coplanar with said one face of said test-piece.

10. Apparatus for measuring the fatigue of a test-piece in bending, said test-piece having at least one flat face and an area of preferred bending for the purpose of bending in a plane at right-angles to said face, comprising two members, means for connection of said members to the test-piece in areas of the latter located respectively on either side of its area of preferred bending, means for imparting to said members a movement of relative rotation along said perpendicular plane for bending the test-piece, means for emitting and means for receiving ultrasonic waves respectively, on either side of the area of preferred bending and in line with the latter, flush with said face, said means for connecting the test-piece to the said members leaving the area of said face located between the said emitter and receiving means free from mechanical stresses, and means connected to said emitter and receiver means for measuring the attenuation of the waves between the latter.

11. Apparatus according to claim 10, in which the means for emitting and the means for receiving the ultrasonic waves comprise, in contact with edges of the test-piece located respectively on either side of the area of preferred bending, two blocks of a piezo-electric material integral with said edges and comprising a face in the same plane as said face, the said blocks comprising on said faces emitter and receiver combs respectively connected to the measurement means and arranged in line with the area of preferred bending, and said blocks of piezo-electric material being free from mechanical stresses.

12. A bench for mounting a said block of piezo-electric material on a test-piece used in the apparatus according to claim 11, said bench comprising two supports respectively for each of the parts to be assembled, leaving said face exposed, at least in the vicinity of the edges to be assembled, means for modifying the relative level and orientation of the supports in order to bring into a coplanar position said flat face of the test-piece and said face of the block of piezo-electric material supporting an emitter or receiver comb respectively, means for moving the supports towards each other at will, in order to bring the said edges of the test-piece and of the block of piezo-electric material into contact, and optical means for controlling the relative level and orientation of said faces at least in the vicinity of the edges to be assembled.

13. Apparatus according to claim 10, in which one of said members is stationary and the other member is movable and supported by the stationary member at one end by means of the test-piece and at the other end, beyond the test-piece with respect to the first member, by a device for imparting a movement to said other member in a direction at right-angles to said face of the test-piece.

* * * * *